United States Patent [19]

Cobb

[11] 4,238,408
[45] Dec. 9, 1980

[54] COMPOUNDS AND PROCESS

[75] Inventor: Raymond L. Cobb, Bartlesville, Okla.

[73] Assignee: Phillips Petroleum Company, Bartlesville, Okla.

[21] Appl. No.: 11,747

[22] Filed: Feb. 13, 1979

[51] Int. Cl.³ .................. C07C 120/00; C07C 121/20
[52] U.S. Cl. .............................. 260/465.8 R; 528/293;
528/337; 528/367; 528/373; 260/464; 260/465
E; 260/465 F; 260/465 H; 260/465.5 R;
260/465.6; 562/594
[58] Field of Search .................... 260/465.8 R, 465 H,
260/465.6, 465 F, 464, 465 E, 465.5 R

[56] References Cited
U.S. PATENT DOCUMENTS

| 3,140,306 | 7/1964 | Heininger | 260/465 G |
|---|---|---|---|
| 3,192,231 | 6/1965 | Welcher | 260/465.9 X |
| 3,541,119 | 11/1970 | Richter et al. | 260/465.8 R X |
| 3,591,621 | 7/1971 | Hutchinson | 260/465.4 |
| 3,842,044 | 10/1974 | Cleary | 260/78 R |
| 3,853,823 | 12/1974 | Cleary | 260/78 R |
| 3,922,250 | 11/1975 | Cleary | 260/49 |
| 3,929,860 | 12/1975 | Drake | 260/464 X |
| 3,931,118 | 1/1976 | Cleary | 260/78 SC |
| 3,951,923 | 4/1976 | Cleary | 260/78 A |
| 3,980,621 | 9/1976 | Campbell et al. | 260/78 R |
| 3,980,695 | 9/1976 | Chabardes et al. | 260/464 X |
| 4,025,493 | 5/1977 | Drake | 260/75 R |

Primary Examiner—Joseph Paul Brust

[57] ABSTRACT

Novel compounds are provided comprising dicyanosulfinates, dicyanosulfonates and dicyanosulfones as well as process of preparing these compounds. These novel compounds are useful in the preparation of monomers for use in polymers, particularly polymers useful in the fibers and textile industry.

14 Claims, No Drawings

COMPOUNDS AND PROCESS

This invention pertains to new compositions of matter and processes of preparing same. In accordance with another aspect, this invention relates to new compositions of matter comprising dicyanosulfinates, dicyanosulfonates and dicyanosulfones. In accordance with a further aspect, this invention relates to the process of preparing dicyanosulfinates by reaction of a 3-cyanosulfolane compound and a cyanide compound in the presence of polar organic diluents. In accordance with another aspect, dicyanosulfonates were prepared from dicyanosulfinates by oxidation of the sulfinate group to the sulfonate group. In accordance with a further aspect, dicyanosulfones are prepared by the reaction of dicyanosulfinates with a hydrocarbyl halide.

It is well known in the textile and fiber industries that functional groups on a polymer chain exhibit a great influence on the properties and the characteristics of the resultant polymers. Characteristics such as dyeability and dye-retention are the subject of a great deal of interest and activity in the fiber industry. Thus, materials which could be employed in the polymerization of monomers to form polymers with dye-receptive sites are of great interest. Such functional groups also frequently influence characteristics such as water absorption and solubility in polar solvents.

This invention pertains to new compositions of matter, dicyanosulfinates, dicyanosulfonates, and dicyanosulfones, which are useful in the preparation of monomers for use in polymers, particularly polymers useful in the fiber and textile industry.

Accordingly, an object of this invention is to provide novel compositions of matter.

A further object of this invention is to provide processes for preparing novel compositions of matter.

A further object of this invention is to provide novel compositions having utility in the preparation of monomers for use in polymers.

Other objects, aspects as well as the several advantages will be apparent to those skilled in the art upon reading the specification and the appended claims.

In accordance with the invention, novel compositions of matter are provided comprising salts of 3,4-dicyanoalkanesulfinic acids, salts of 3,4-dicyanoalkanesulfonic acids, and hydrocarbyl 3,4-dicyanoalkanesulfones.

Further in accordance with this invention, salts of 3,4-dicyanoalkanesulfinic acids are prepared by reaction of a 3-cyanosulfolane compound and a cyanide compound in the presence of polar organic diluents.

In accordance with another embodiment of the invention, salts of 3,4-dicyanoalkanesulfonic acids are prepared by the oxidation of salts of 3,4-dicyanoalkanesulfinic acids.

In accordance with another embodiment of the invention, hydrocarbyl 3,4-dicyanoalkanesulfones are prepared by the reaction of salts of 3,4-dicyanoalkanesulfinic acids and a hydrocarbyl halide.

In accordance with a specific embodiment, the invention comprises novel compounds including sodium 3,4-dicyanobutane-1-sulfinate, sodium 3,4-dicyanobutane-1-sulfonate and 2-(2-methylsulfonylethyl)succinonitrile.

The novel compositions of matter of this invention are salts of 3,4-dicyanoalkanesulfinic acid, salts of 3,4-dicyanoalkanesulfonic acid, and hydrocarbyl 3,4-dicyanoalkanesulfones generally corresponding to the following formulas I, II, and III, respectively:

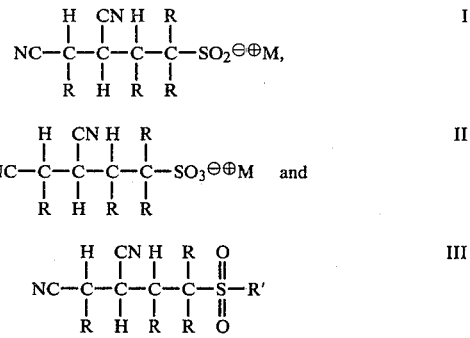

wherein R is independently selected from hydrogen, hydrocarbyl groups or alkoxy-substituted hydrocarbyl groups containing from 1 to about 6 carbon atoms per group, R' is a hydrocarbyl group containing 1 to 7 carbon atoms, with the further proviso that the total number of carbon atoms in molecules of formulas I, II, and III will not exceed 13, and M is an alkali metal or a quaternary ammonium group having up to and including 6 carbon atoms.

Exemplary R groups suitable for the above formulas include methyl, ethyl, n-propyl, isopropyl, n-butyl, amyl, n-hexyl, cyclopentyl, cyclohexyl, phenyl, methoxymethyl, 2-ethoxyethyl, and the like.

Suitable R' groups for the above formulas include methyl, ethyl n-propyl, isopropyl, n-butyl, amyl, n-hexyl, cyclopentyl, cyclohexyl, phenyl, benzyl, p-tolyl, and the like.

The M groups of the above formulas are exemplified by lithium, sodium, potassium, rubidium, cesium, tetramethylammonium, and the like.

The inventive compositions of formula I are readily prepared by reaction of a 3-cyanosulfolane compound (formula IV)

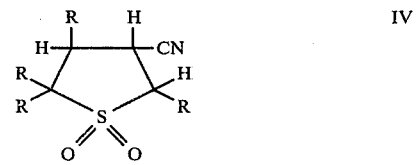

and cyanide compound of formula MCN wherein M is as described above in the presence of polar organic diluents. R groups in formula IV correspond to the R groups in formulas, I, II, and III.

The conditions under which reaction between the 3-cyanosulfolane compound and cyanide compound takes place is, of course, very dependent upon the reactivity of the starting materials. Temperatures generally in the range of 25° to 200° C. will provide the desired results, however, it is generally preferred to employ temperatures in the range of 75° to 150° C. The reaction time is highly dependent upon the reactivity of the reactants and the temperature employed, however, generally reaction times of from several minutes to several days provide the desired results.

The amounts of reactants employed to prepare the compounds of formula I can vary widely depending upon the desired degree of conversion of either reactant, however, generally the use of from 0.1 to 10 moles of cyanide compound per mole of 3-cyanosulfolane compound is suitable for obtaining the desired results. It is preferred, however, to employ from 0.25 to 1 mole of cyanide compound per mole of 3-cyanosulfolane compound.

Diluents which are suitable for use in the preparation of compounds of formula I are generally any of the well known polar organic solvents which do not contain active hydrogens. Exemplary solvents include diethyl ether, tetrahydrofuran, N,N-dimethylformamide, dimethylsulfoxide, triethylamine, glyme, diglyme, triglyme, and the like.

Compounds of formula II are readily prepared from the compounds of formula I by oxidation of the sulfinate group to the sulfonate group of formula II. It is well within the knowledge of one of average skill in organic chemistry to select oxidizing materials and conditions for the conversion of sulfinate groups to sulfonate groups. For example, air, oxygen gas, and the like will cause the desired conversion. Reaction conditions are highly dependent upon the reactivity of the dicyanosulfinate compound and the appropriate oxidizing agent. Any of the polar organic solvents useful in the preparation of the compounds of formula I are likewise useful in the oxidation of compounds of formula I to compounds of formula II. Reaction temperatures will generally be in the range of 0° C. to 100° C. for whatever time is required to produce the desired degree of conversion. Usually contacting reactants for from several seconds to several hours produces the desired reaction to the desired degree.

Compounds of formula III are readily prepared from compounds of formula I by any of the means which are well known in the art for the conversion of sulfinates to sulfones. For example, reaction of a hydrocarbyl halide of formula R'X wherein R' is as described above and X is chloride, bromide, or iodide, with compounds of formula I will produce the desired hydrocarbyl dicyanosulfones of formula III. Reaction conditions for conversion of the sulfinates to sulfones will again be highly dependent upon the reactivity of the reactants. Temperatures in the range of from about 25° C. to about 200° C. are appropriate for the desired conversion, though temperatures in the range of 50° C. to 125° C. are generally preferred. The reaction times will generally be whatever is needed to produce the desired degree of conversion, for example, from several minutes to 24 hours.

Isolation and purification of the inventive compositions of matter can be accomplished by any of the means well known in the art, such as, filtration, recrystallization, solvent extraction, and the like.

The conversion of the compounds of formulas I, II, and III to compounds suitable for use in the preparation of polymers is accomplished by means which are well known in the art for converting nitrile groups to groups such as amine or carboxylic acid. The art contains many references to the catalytic hydrogenation of nitrile groups to primary amines over a wide variety of catalysts, such as, platinum, palladium, rhodium, Raney nickel, and the like. Acid-or base-catalyzed hydrolysis reactions for the conversion of nitriles to carboxylic acids are likewise well known in the art. The conversion of the nitrile groups of formulas I, II, and III to give diamine compounds or dicarboxylic acids provides materials which are readily polymerizable to give polyesters, polyamides, polyureas, and the like, which are believed to be useful in the fiber and textile industries.

EXAMPLE I

The following runs demonstrate the reaction of 3-cyanosulfolane with sodium cyanide to give sodium 3,4-dicyanobutane-1-sulfinate which was then either oxidized to sodium 3,4-dicyanobutane-1-sulfonate or converted by reaction with methyl iodide to the corresponding methylsulfone, i.e., 2-(2-methylsulfonylethyl)-succinonitrile.

Preparation of 3-cyanosulfolane to be used in reaction with sodium cyanide was accomplished by stirring under reflux conditions for 24 hours a solution of 2-sulfolene (100 gm), acetone cyanohydrin (125 gm) and potassium cyanide (65 gm) in acetone (600 ml). The reaction mixture was filtered, acidified with acetic acid (40 ml), treated with charcoal, filtered, concentrated to 300 ml, and cooled to 20° C. The resultant solid (87.6 gm) was separated and identified as 3-cyanosulfolane by comparison of infrared and nmr spectra and melting point with those given in the literature.

A solution of 3-cyanosulfolane (2.5 gm) and sodium cyanide (0.3 gm) in N,N-dimethylformamide (25 ml) under an atmosphere of nitrogen was heated at 100° C. for 24 hours. After removal of the solvent under vacuum the residue was dissolved in acetone (30 ml). After filtering the resultant solution to remove turbidity and cooling the filtrate to −70° C., unreacted 3-cyanosulfolane (1.14 gm) was removed by filtration. The resulting filtrate was stripped of solvent under vacuum and the residue was again dissolved in acetone (30 ml). Tetrahydrofuran was added slowly at room temperature with stirring to the acetone solution until a cloud point was reached. Subsequent cooling of the cloudy solution to −70° C. resulted in precipitation of a white solid, filtration and vacuum drying of which yielded 1.12 gm of white powder identified as sodium 3,4-dicyanobutane-1-sulfinate. Major definitive infrared absorption bands (KBr pellet) occurred at 9.8 and 10.4μ.

Double recrystallization and subsequent drying under vacuum of the thus-obtained sodium 3,4-dicyanobutane-1-sulfinate using acetone-ethyl acetate (adding ethyl acetate to an acetone solution cooled to −70° C. then slowly warming to room temperature-note inverse solubility characteristics) yielded sodium 3,4-dicyanobutane-1-sulfonate analytical data of which are recorded in Table I. Apparently the original reaction product, sodium 3,4-dicyanobutane-1-sulfinate, was oxidized during the purification process to the more stable sulfonate.

TABLE I

| Sodium 3,4-Dicyanobutane-1-sulfonate | | | | | |
|---|---|---|---|---|---|
| Infrared absorption[1] | 4.4μ(CN), 8.3 and 9.5μ(—$SO_3^-$) | | | | |
| $^1$H NMR[2] | 3.1–3.8 (multiplet, $CH_2SO_3$), 2.95–3.2 (doublet + multiplet, $CH_2$—CN, CH—CN), 2.2 (multiplet, $CH_2$) | | | | |
| $^{13}$C NMR[3] | 191.1 (NC—CH), 121.3 (NC—$CH_2$), 49.1 ($CH_2$—$SO_3$—), 28.4 (CH), 27.6 (—CH—$CH_2$—$CH_2$—), 21.4 (NC—$CH_2$) | | | | |
| Elemental analysis | C | H | N | Na | S |
| Calculated for $C_6H_7N_2NaO_3S \cdot 2H_2O$ | 29.26 | 4.50 | 11.38 | 9.34 | 13.02 |

TABLE I-continued

| Sodium 3,4-Dicyanobutane-1-sulfonate | | | | | |
|---|---|---|---|---|---|
| Found | 28.8 | 3.6 | 10.7 | 10.1 | 13.3 |

[1] Major definitive absorbances - measured in KBr pellet.
[2] Major absorbances (measured in $D_2O$) expressed in parts per million downfield from tetramethylsilane as an internal standard.
[3] Major absorbances (measured in $D_2O$) expressed in parts per million downfield from tetramethylsilane as an external standard.

In the following run, sodium 3,4-dicyanobutane-1-sulfinate was converted to the corresponding methyl sulfone to verify the structure assignment of the above-described reaction product.

A solution of 3-cyanosulfolane (3.0 gm) and sodium cyanide (1.0 gm) in N,N-dimethylformamide (50 ml) under nitrogen was stirred at 55° C. for 24 hours. After the solvent was stripped under vacuum, the residue was dissolved in tetrahydrofuran (about 30 ml). The tetrahydrofuran solution was cooled to −70° C. and diethyl ether was added to the cloud point. Allowing the resulting solution to warm to room temperature, followed by filtration and drying of the precipitate under vacuum yielded a white solid (3.5 gm). A mixture of the thus-recovered solid (3.5 gm), methyl iodide (5 ml) and methanol (150 ml) was heated at 100° C. for 4 hours after which volatiles were removed under vacuum. Workup of the resulting dark residue by dissolution in tetrahydrofuran/methylene chloride (2:1 volume ratio), washing with saturated aqueous sodium thiosulfate, drying over magnesium sulfate, stripping of volatiles under vacuum and two recrystallizations from acetone gave 2-(2-methylsulfonylethyl)succinonitrile (1.2 gm, m.p. 123°–125° C.) analytical data of which are given in Table II.

TABLE II

| 2-(2-Methylsulfonylethyl)succinonitrile | |
|---|---|
| Infrared absorption[1] | 4.4(CN), 7.7 and 8.8($SO_2$) |
| $^1$H NMR[2] | 2.7–3.5(multiplets, NC—$CH_2$—CH—, —$CH_2$—$SO_2$) |
| | 3.07(singlet,$CH_3$), 2.1–2.5 (multiplet, CH—$CH_2$—$CH_2$) |
| $^{13}$C NMR[3] | 118.6(NC—$CH_2$), 116.5(NC—CH), 52.6 ($CH_2$—$SO_2$), 41.7($CH_3$), 29.0(CH), 25.2(CH—$CH_2$—$CH_2$), 21.4(NC—$CH_2$). |

| Elemental analysis | C | H | N | S |
|---|---|---|---|---|
| Calculated for $C_7H_{10}N_2O_2S$ | 45.14 | 5.41 | 15.04 | 17.22 |
| Found | 45.6 | 5.3 | 15.2 | 17.0 |

[1] Major definitive absorbances in microns, measured in KBr pellet.
[2] Major absorbances (measured in $D_2O$)expressed in parts per million downfield from tetramethylsilane as an internal standard.
[3] Major absorbances (measured in $D_2O$) expressed in parts per million downfield from tetramethylsilane as an external standard.

Thus identification of the product from the reaction of the above-described reaction product with methyl iodide verified the structure assignment of the product of the reaction of 3-cyanosulfolane with sodium cyanide.

I claim:

1. Salts of 3,4-dicyanoalkanesulfinic acid and 3,4-dicyanoalkanesulfonic acid and hydrocarbyl 3,4-dicyanoalkanesulfones which correspond, respectively, to the following formulas

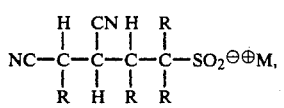   I

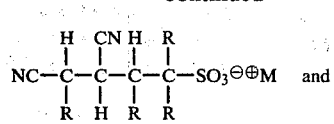   II

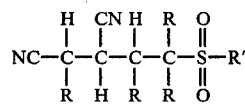   III wherein R is independently selected from hydrogen, alkyl, cycloalkyl and phenyl groups or alkoxy-substituted alkyl and cycloalkyl groups containing from 1 to about 6 carbon atoms per group, R' is an alkyl, cycloalkyl, phenyl, benzyl, or p-tolyl radical containing 1 to 7 carbon atoms, with the further proviso that the total number of carbon atoms in molecules of formulas I, II, and III will not exceed 13, and M is an alkali metal or a quaternary ammonium group having up to and including 6 carbon atoms.

2. A compound according to claim 1 which is a dicyanosulfinate of formula I.

3. A compound according to claim 1 which is a dicyanosulfonate of formula II.

4. A compound according to claim 1 which is a dicyanosulfone of formula III.

5. A salt of 3,4-dicyanoalkanesulfinic acid according to claim 2 which is sodium 3,4-dicyanobutane-1-sulfinate.

6. A salt of 3,4-dicyanoalkanesulfonic acid according to claim 3 which is sodium 3,4-dicyanobutane-1-sulfonate.

7. A hydrocarbyl 3,4-dicyanoalkanesulfone according to claim 4 which is 2-(2-methylsulfonylethyl)succinonitrile.

8. The process for the preparation of salts of 3,4-dicyanoalkanesulfinic acids according to claim 2 which comprises reacting a 3-cyanosulfolane compound with an alkali metal cyanide or quaternary ammonium cyanide in the presence of a polar organic diluent under conditions which produce compounds of formula I.

9. A process according to claim 8 wherein the temperature for said reaction is in the range of 25°–200° C., the amount of cyanide present ranges from 0.1 to 10 moles per mole of sulfolane, and the polar diluent is selected from diethyl ether, tetrahydrofuran, N,N-dimethylformamide, dimethylsulfoxide, triethylamine, glyme, diglyme, triglyme, and the like.

10. A process according to claim 8 for producing sodium 3,4-dicyanobutane-1-sulfinate which comprises reacting 3-cyanosulfolane with sodium cyanide in the presence of N,N-dimethylformamide.

11. A process for the conversion of dicyanosulfinates to the corresponding dicyanosulfonates which comprises oxidizing the sulfinate group in a compound having formula I as defined in claim 1 to the sulfonate group in a compound having formula II as defined in claim 1.

12. A process according to claim 11 for the production of sodium 3,4-dicyanobutane-1-sulfonate which comprises oxidizing sodium 3,4-dicyanobutane-1-sulfinate.

13. A process for the conversion of dicyanosulfinates of formula I defined in claim 1 to the corresponding dicyanosulfones of formula III defined in claim 1 which comprises reacting a dicyanosulfinate as defined in formula I with a hydrocarbyl halide of the formula R'X wherein R' is a hydrocarbyl group containing 1 to 7 carbon atoms and X is chloride, bromide or iodide under conditions which produce compounds of formula III.

14. A process according to claim 13 for the production of 2-(2-methylsulfonylethyl)succinonitrile which comprises reacting sodium 3,4-dicyanobutane-1-sulfinate with methyl iodide.

* * * * *